US00PP23241P2

(12) United States Plant Patent
Korlipara

(10) Patent No.: US PP23,241 P2
(45) Date of Patent: Dec. 4, 2012

(54) ***ECHINACEA* PLANT NAMED 'QUILLS AND THRILLS'**

(50) Latin Name: *Echinacea purpurea*
Varietal Denomination: Quills and Thrills

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 46 days.

(21) Appl. No.: 13/134,687

(22) Filed: Jun. 9, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — Susan McCormick Ewoldt
(74) *Attorney, Agent, or Firm* — Klarquist Sparkman, LLP

(57) ABSTRACT

A new and distinct *Echinacea* plant named 'Quills and Thrills' characterized by large inflorescences with quilled ray florets of purple pink, a compact, multicrown habit, a long bloom time, and excellent vigor.

2 Drawing Sheets

Botanical denomination: *Echinacea purpurea.*
Variety designation: 'Quills and Thrills'.

The present invention relates to a new and distinct cultivar of *Echinacea purpurea* and given the cultivar name 'Quills and Thrills'. *Echinacea* is in the family Asteraceae. This new cultivar originated from a planned breeding program for a quilled *Echinacea*. The parents were unnamed, proprietary, unreleased plants. The exact parents are unknown.

Compared to *Echinacea* purpurea 'All That Jazz' (U.S. Plant Pat. No. 21,771), the new cultivar has larger flowers, a shorter, denser habit, with much more uniformly quilled flowers, and it is more free-flowering.

This new *Echinacea* cultivar is distinguished by:

1. large inflorescences with quilled ray florets of purple pink,
2. a compact, multicrown habit,
3. a long bloom time,
4. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
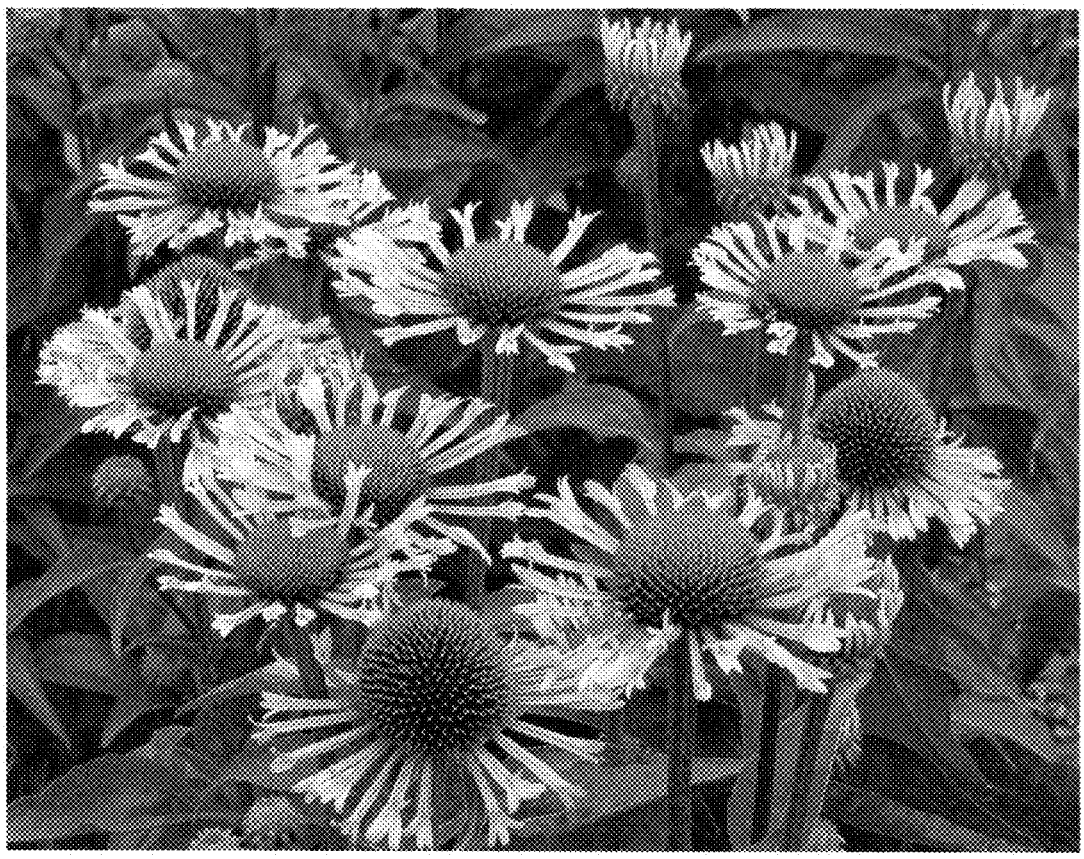
FIG. 1 shows a close up of the flowers of *Echinacea* 'Quills and Thrills' on a nine-month-old plant growing in full sun in the in late August in Canby, Oreg.
Figure 2:
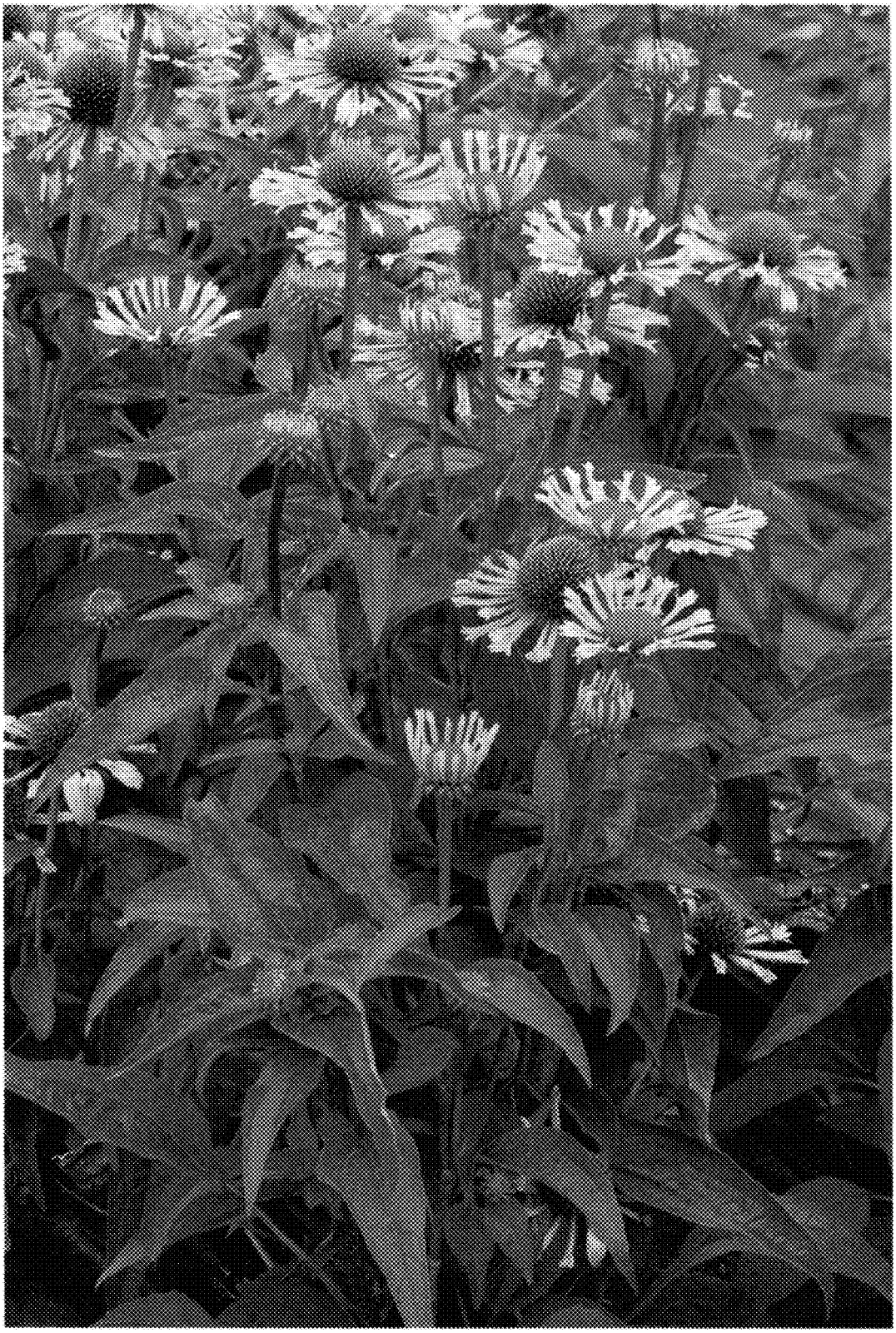
FIG. 2 shows the whole *Echinacea* 'Quills and Thrills' plant.

The following is a detailed description of the new *Echinacea* cultivar based on observations of one and a half year-old specimens growing in two-gallon containers forced in a greenhouse for May flowering in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type.*—Herbaceous perennial.
*Hardiness.*—USDA Zones 4 to 9.
*Size.*—66 cm wide and grows to 69 cm tall to top of flowers.
*Form.*—Basal clump.
*Number of crowns.*—23.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending.
*Number of flowering stems from the ground.*—18.
*Size.*—Branching to 45 cm tall to a terminal flower and 4 mm wide at base.
*Internode length.*—4 cm to 16 cm.
*Surface texture.*—Strigose.
*Color.*—Yellow Green 146A tinted and/or speckled with Greyed Purple 187A.

Leaf (basal):

*Type.*—Simple.
*Shape.*—Ovate.
*Arrangement.*—Basal.
*Blade size.*—Grows to 19 cm long and 8.5 cm wide.
*Margins.*—Serrate.
*Apex.*—Acute.
*Base.*—Attenuate.
*Surface texture.*—Strigose on both sides.
*Venation.*—Pinnate.
*Color.*—Topside, Green N137A, bottom side Green N137B.

*Petiole description*.—Grows to 28 cm long and 6 mm wide (at base), strigose, Yellow Green 146C except topside inside petiole furrow and bottom ¼ where Greyed Purple 187A.

Leaf (stem):

*Type*.—Simple.

*Shape*.—Lanceolate.

*Arrangement*.—Alternate.

*Blade size*.—Grows to 12.5 cm long and 5 cm wide.

*Margins*.—Serrate.

*Apex*.—Acuminate.

*Base*.—Attenuate.

*Surface texture*.—Strigose on both sides.

*Venation*.—Pinnate, with 3 main veins from the base.

*Color*.—Topside, Green N137A; bottom side Green N137B.

*Petiole description*.—On lowermost leaves, clasping, grows to 5 cm long and 2 mm wide above the clasp, strigose, Yellow Green 146B.

Inflorescence:

*Type*.—Composite on terminal stalked heads.

*Size*.—Grows to 10.5 cm wide and 2.5 cm deep as disc enlarges.

*Form*.—Ray petals held horizontally, mature disc is conic.

*Immature inflorescence*.—Grows to 2.7 cm wide and 2.4 cm deep, ray florets held upright and rolled up so only the back color shows, Red Purple N57D with tips Yellow Green 146C, disc background is Yellow Green 146B, foreground is Greyed Orange 172A.

*Ray florets*.—Without pistil or stamen, 17 to 24 in number, grows to 45 mm long and 13 mm wide; tubular with the lobes variable, usually 2 lobed but may be emarginated to 4 lobed, glabrous on both sides; tube 29 mm long; topside color Red Purple 71A on tube and 70B on lobes, bottom side Red Purple 71A on tube to Greyed Purple 186B on lobes.

*Disc*.—Flat becoming conic, becoming 19 mm deep and 30 mm wide with maturity, overall color Greyed Purple N186C.

*Disc florets*.—About 200 in number, 10 mm long and 2 mm wide, each with one persistent, very stiff bract (12 mm long, Greyed Purple 187A on tip, the top 2 mm Yellow Orange 22A, rest Yellow Green 146B); corollas 6 mm long and 2 mm wide, tubular with 5 lobes, each 1 mm long and 1 mm wide, glabrous, tip acute, margin entire, tube color Yellow Green 147D on bottom half, top half and lobes Greyed Red 178A; pistil 11 mm long, ovary 4 mm long, White 155B, style 4 mm long White 155B, 2-branched stigma spreading 1.2 mm wide, tinted Greyed Purple 187B; stamen 4 in number, 6 mm long, anthers 3 mm long and Black 202A, filaments 3 mm long, Yellow Orange 19D, pollen Yellow 21A.

*Phyllaries*.—In 4 leafy series, area 3 cm wide and 10 mm deep, lobes lanceolate in shape, reflexed, grow to 8 mm long and 2.5 mm wide, Green N137B, margins strigose, tip acute, strigose on both sides.

*Receptacle*.—Grows to 10 mm wide and 9 mm deep, White NN155A.

*Bloom period*.—July through October in Canby, Oreg.

*Fragrance*.—Light, floral.

*Lastingness*.—Each inflorescence lasts about two weeks in Canby, Oreg.

Seeds: 3 mm long and 2.5 mm wide, oval, Brown 200C.

*Fertility*.—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

* * * * *